(12) United States Patent
Zhang

(10) Patent No.: US 12,151,976 B2
(45) Date of Patent: Nov. 26, 2024

(54) CONCRETE FORMULATION SYSTEM FOR REPAIRING CULTURAL RELIC BUILDING AND USE METHOD THEREOF

(71) Applicant: Yihong Zhang, Guangdong (CN)

(72) Inventor: Yihong Zhang, Guangdong (CN)

(*) Notice: Subject to any disclaimer, the term of this patent is extended or adjusted under 35 U.S.C. 154(b) by 494 days.

(21) Appl. No.: 17/763,819

(22) PCT Filed: Sep. 26, 2020

(86) PCT No.: PCT/CN2020/117955
§ 371 (c)(1),
(2) Date: Mar. 25, 2022

(87) PCT Pub. No.: WO2021/057935
PCT Pub. Date: Apr. 1, 2021

(65) Prior Publication Data
US 2022/0332647 A1  Oct. 20, 2022

(30) Foreign Application Priority Data
Sep. 27, 2019  (CN) .......................... 201910927349.2

(51) Int. Cl.
| | |
|---|---|
| *C04B 28/18* | (2006.01) |
| *C04B 28/04* | (2006.01) |
| *C04B 111/54* | (2006.01) |
| *C04B 111/72* | (2006.01) |
| *G16C 20/90* | (2019.01) |
| *G16C 60/00* | (2019.01) |

(52) U.S. Cl.
CPC ............ *C04B 28/184* (2013.01); *C04B 28/04* (2013.01); *G16C 20/90* (2019.02); *G16C 60/00* (2019.02); *C04B 2111/547* (2013.01); *C04B 2111/72* (2013.01)

(58) Field of Classification Search
CPC . C04B 28/184; C04B 28/04; C04B 2111/547; C04B 2111/72; G16C 20/90; G16C 60/00; G16C 20/40; Y02W 30/91
See application file for complete search history.

(56) References Cited

FOREIGN PATENT DOCUMENTS

| | | | | |
|---|---|---|---|---|
| CN | 101844899 A | * | 9/2010 | ............ C04B 28/12 |
| CN | 101864843 A | | 10/2010 | |
| CN | 106116424 A | * | 11/2016 | ............ C04B 28/26 |
| CN | 106927776 A | | 7/2017 | |
| CN | 108386000 A | | 8/2018 | |
| CN | 108439931 A | | 8/2018 | |
| CN | 109231915 A | | 1/2019 | |
| CN | 110627437 A | | 12/2019 | |
| DE | 4325829 C1 | | 3/1995 | |
| JP | 2006124216 A | | 5/2006 | |

OTHER PUBLICATIONS

International Search Report for PCT/CN2020/117955, mailed Nov. 27, 2020 (8 pages).
Written Opinion for PCT/CN2020/117955, mailed Nov. 27, 2020 (7 pages).

* cited by examiner

*Primary Examiner* — Eman A Alkafawi
*Assistant Examiner* — Dilara Sultana
(74) *Attorney, Agent, or Firm* — Quarles & Brady LLP

(57) ABSTRACT

A concrete formulation system for repairing a cultural relic building and a use method thereof. The method includes obtaining a first index value, a second index value, and a third index value of a cultural relic building concrete sample and comparing the index values in a database of the concrete formulation system to obtain raw material components and contents of an original preparation formula of cultural relic concrete. The method further includes preparing a repairing concrete sample, measuring the index values, of the repairing concrete sample and comparing the index values of the cultural relic building concrete sample, and if the result is that the difference between the first index values is not greater than 20%, the difference between the second index values is not greater than 60%, and the difference between the third index values is not greater than 60%, using the repairing concrete sample for cultural relic repair.

5 Claims, No Drawings

CONCRETE FORMULATION SYSTEM FOR REPAIRING CULTURAL RELIC BUILDING AND USE METHOD THEREOF

CROSS REFERENCE TO RELATED APPLICATIONS

The present application is a national phase entry under 35 USC § 371 of International Application PCT/CN2020/117955, filed Sep. 26, 2020, which claims the benefit of and priority to Chinese Patent Application No. 2019109273492, filed Sep. 27, 2019, the entire disclosures of which are incorporated herein by reference.

TECHNICAL FIELD

The present invention relates to the field of restoration technology of cultural relic, and more particularly, to a concrete formulation system for repairing a cultural relic building and a use method thereof.

BACKGROUND

A cultural relic building is generally repaired with "a original material by an original workmanship" to maintain "cultural importance", and the original old material of the cultural relics building or materials made by original workmanship shall be used as far as possible. The concrete material (including mortar or plaster) of the cultural relic building is a kind of building material made of multi formula and multi raw materials through mixing, calcination, combination and solidification. At present, it is difficult or impossible to retrieve the materials produced by the original workmanship and find the original old material. Therefore, when repairing the cultural relic building with the concrete material, the repair material with a workability, a durability, a mechanical property and a chemical property similar to those of the original old material should be used as much as possible to restore the formula of the original old material. In the prior art, when preparing the repair material of the concrete material, generally only the compressive strength, setting time and dry shrinkage resistance of the repair materials are considered (whether they have the characteristics of high strength, fast hardening and less dry shrinkage), but the reduction of the original materials of cultural relics concrete is not considered, resulting in a large difference in the chemical composition, physical properties and other indexes between the concrete used for repair and the cultural relics concrete materials, the restoration degree is low, so it is difficult to achieve the purpose of repairing with "a original material by an original workmanship" to maintain "cultural importance".

The CN application No. 201810267192.0, titled MARL FOR REPAIRING THE DECORATION OF MODERN CULTURAL RELIC BUILDING, discloses a marl formula comprising water, fly ash, quicklime, washed medium sand, active silica, active calcium oxide, silicic acid, calcium bicarbonate and titanium oxide. The formula is mainly aimed at a marl with more washed-out sand, but it cannot be prepared for marl with more silicate, carbonate or calcium hydroxide, which limits the use of the formula.

On the other hand, in the prior art, the restoration degree of the original old material is low, the content of each compound component in the original old material is generally only determined by some spectral detection and analysis or chemical analysis methods, and mixing and preparation are performed with an existing material. However, with the passage of time, the original material of the same kind or name is quite different from the existing material, for example, former cement clinker is different from existing cement clinker. Due to different manufacturing processes of a former cement clinker and an existing cement clinker, the produced cement clinkers have certain differences in physical property, chemical properties and chemical composition, so that the cement clinker in the existing material cannot be used to really reduced to the cement clinker in the old material. Therefore, determining the content of each compound component in the original old material only cannot realize the restoration of the old material, so that the purpose of repairing with "a original material by an original workmanship" and maintaining "cultural importance" cannot be achieved.

Therefore, the prior art has the defects and needs to be improved.

SUMMARY

The present invention aims to overcome the defects in the prior art, and provide a concrete formulation system for repairing a cultural relic building and a use method thereof, so that a problem that marl (or concrete) containing more silicate, more carbonate, more hydroxide, more fly ash, or more quicklime cannot be prepared in the prior art is solved; and meanwhile, a problem that the material formula of original old material cannot be restored, leading to the failure to achieve the cultural relic protection purpose of repairing with "a original material by an original workmanship" and maintaining "cultural importance", is solved.

The technical solutions of the present invention are as follows: a concrete formulation system for repairing a cultural relic building and a use method thereof are provided, wherein the concrete formulation system consists of a solid phase and a water phase, and the solid phase and the water phase are mixed according to a mass percentage ratio of 1:0.5-2; the solid phase consists of a gel matrix and an additive, comprising 0.1% to 99.9% of gel matrix and 99.9% to 0.1% of additive, wherein the gel matrix is at least one selected from the group consisting of cement, volcanic ash, fly ash, gypsum, silica fume, kaolin, metakaolin, diatomite, slag powder, siliceous slag powder and burnt clay; and the additive comprises at least one selected from the group consisting of lime, aggregate, active silica, active calcium oxide, active magnesium oxide, calcium bicarbonate, silicic acid and titanium oxide; and the use method comprises the following steps of:

S1: obtaining a cultural relic building concrete sample;

S2: obtaining a first index value of the cultural relic building concrete sample, wherein the first index value is a mass percentage value of silicate and/or hydroxide and/or carbonate and/or sulfate and/or ferraluminate and/or aluminate and/or sulfoaluminate and/or chloride in concrete detected and analyzed by a spectrum analyzer;

S3: obtaining a second index value of the cultural relic building concrete sample, wherein the second index value is a chloride ion migration coefficient and/or an average carbonization degree value and/or a mass percentage value of oxide of concrete detected and analyzed by a chemical analysis method;

S4: obtaining a third index value of the cultural relic building concrete sample, wherein the third index value is a strength value and/or an early strength value and/or a porosity and/or an elasticity value and/or a creep value and/or a volume change value and/or a frost resistance value and/or an average water penetration height value of concrete detected and analyze by a mechanical analysis method;

S5: comparing the first index value, the second index value, and the third index value of the cultural relic building concrete sample with a first index value, a second index value, and a third index value in a database of the concrete formulation system, when the first index value, the second index value and the third index value of the concrete formula obtained from the database of the concrete formula system are not more than 20% different from the first index value, the second index value and the third index value of the concrete sample of cultural relics, the raw material composition and content of the corresponding concrete formula are recorded. The raw material composition and content of the corresponding concrete formula is the raw material composition and content of the cultural relics building concrete sample;

S6: according to the raw material components and contents of the cultural relic concrete obtained in step S5, using materials of the concrete formulation system to prepare a repairing concrete sample;

S7: respectively detecting and analyzing the first index value, the second index value, and the third index value of the repairing concrete sample by the spectrum analyzer, the chemical analysis method, and the mechanical analysis method, and comparing and analyzing the first index value, the second index value, and the third index value of the repairing concrete sample with the first index value, the second index value, and the third index value of the cultural relic building concrete sample detected and analyzed in step S2 to step S4;

S8: if comparison and analysis results are that a difference between the first index values of the repairing concrete sample and the cultural relic building concrete sample is greater than 20% and/or a difference between the second index values is greater than 60% and/or a difference between the third index values is greater than 60%, then according to the concrete formulation system, adjusting material components and mass percentages of the repairing concrete sample, preparing the repairing concrete sample with the adjusted material components and contents, and repeating step S7; and S9: if comparison and analysis results are that a difference between the first index values of the repairing concrete sample and the cultural relic building concrete sample is not greater than 20%, a difference between the second index values is not greater than 60%, and a difference between the third index values is not greater than 60%, using the repairing concrete sample for cultural relic repair.

Standard operation steps of the spectrum analyzer, the chemical analysis method and the mechanical analysis method may refer to standard operations in *Methods for Chemical Analysis of Cement and Standard for Test Methods of Long-term Performance and Durability of Ordinary Concrete*.

Further, the solid phase consists of 0.1% to 99.9% of gel matrix, 0.01 wt % to 85 wt % of lime, 0.01 wt % to 70 wt % of aggregate, 0.01 wt % to 40 wt % of active silica, 0.01 wt % to 30 wt % of active calcium oxide, 0.01 wt % to 5 wt % of active magnesium oxide, 0.01 wt % to 20 wt % of calcium bicarbonate, 0.01 wt % to 10 wt % of silicic acid, and 0.01 wt % to 10 wt % of titanium oxide. During the preparation of repairing concrete, 0.01 wt %~40 wt % active silica, 0.01 wt %~30 wt % active calcium oxide, 0.01 wt %~5 wt % active magnesium oxide and 0.01 wt %~10 wt % titanium oxide are added to adjust the contents of silicon compounds, calcium compounds, magnesium compounds and titanium compounds in the prepared repairing concrete. Adding 0.01 wt %~10 wt % silicic acid can adjust the content of silicate and silica in the prepared repairing concrete, and adding 0.01 wt %~20 wt % calcium bicarbonate can promote the carbonization of calcium compounds in the preparation process of repairing concrete, and adjust the content of carbonate in the prepared repairing concrete, so that the first index value, the second index value and the third index value of the prepared repairing concrete sample are closer to the first index value, the second index value and the third index value of the cultural relics building concrete sample. As for the database for manufacturing the concrete formulation system, the database comprises the first index value, the second index value, and the third index value; the first index value is the mass percentage value of silicate and/or hydroxide and/or carbonate and/or sulfate and/or ferraluminate and/or aluminate and/or sulfoaluminate and/or chloride in concrete detected and analyzed by the spectrum analyzer; the second index value is the chloride ion migration coefficient and/or the average carbonization degree value and/or the mass percentage value of oxide of concrete detected and analyzed by the chemical analysis method; and the third index value is the strength value and/or the early strength value and/or the porosity and/or the elasticity value and/or the creep value and/or the volume change value and/or the frost resistance value and/or the average water penetration height value of concrete detected and analyze by the mechanical analysis method.

Further, the aggregate is at least one selected from the group consisting of washed-out medium sand, washed-out coarse sand and stone chip.

Further, the spectrum analyzer is an XRF analyzer or an X-ray diffractometer or a laser-induced breakdown spectrometer or a Raman spectrometer; the chemical analysis method is an ignition subtraction method or a titration method or a rapid determination method of chloride ion diffusion coefficient of concrete and a phenolphthalein test method; and the mechanical analysis method is a shear compression method or a creep test method or a water penetration height method.

Further, the active silica is nano silica, and the active calcium oxide is nano calcium oxide.

By using the technical solutions above, the present invention provides the concrete formulation system for repairing the cultural relic building and the use method thereof. The first index value, the second index value, and the third index value of the cultural relic building concrete sample are detected by the spectrum analyzer, the chemical analysis method, and the mechanical analysis method respectively, detected results of the first index value, the second index value, and the third index value are compared with data in the database of the concrete formulation system. When the difference between the first index value, the second index value and the third index value of the concrete formula obtained from the database of the concrete formula system and the first index value, the second index value and the third index value of the concrete sample of the cultural relics building is no more than 20%, the raw material composition and content of the corresponding concrete formula are recorded. The raw material composition and content of the corresponding concrete formula is the raw material composition and content of the cultural relics building concrete sample, so as to restore the raw material of the concrete sample of the cultural relic building, and further prepare the repairing concrete sample according to the raw material component and content of the obtained corresponding concrete formula. After preparing the repairing concrete sample, the first index value, the second index value, and the third index value of the repairing concrete sample are further detected by the spectrum analyzer, the chemical analysis method, and the mechanical analysis method. The first index value, the second index value, and the third index value obtained are compared and analyzed with the first index value, the second index value, and the third index value of the cultural relic building concrete sample. If the comparison results are that the difference between the first index values of the repairing concrete sample and the cultural relic building concrete sample is greater than 20% and/or the difference between the second index values is greater than 60% and/or the difference between the third index values is greater than 60%, it is indicated that components and properties of the repairing concrete sample quite different from those of the cultural relic building concrete sample. The mass percentages of the raw material components in the repairing concrete sample shall be adjusted to prepare the repairing concrete sample with the adjusted raw material components. If the comparison results are that the difference between the first index values of the repairing concrete sample and the cultural relic building concrete sample is not greater than 20%, the difference between the second index values is not greater than 60%, and the difference between the third index values is not greater than 60%, it is indicated that the prepared repairing concrete sample meets requirements, and has components and properties similar to those of the cultural relic building concrete sample, and the repairing concrete sample may be used to repair a cultural relic corresponding to the cultural relic building concrete sample, so that a raw material formula of an original old material is restored, and a purpose of repairing with "a original material by an original workmanship" and maintaining "cultural importance" is achieved. The solid phase and the water phase are mixed at the mass percentage ratio of 1:0.5-2, hydrated calcium silicate is quickly produced among the active silica, the active calcium oxide, and water, and hardened and shrunk to form a hardened framework, the hardened framework may limit air shrinkage of hydrated calcium silicate, hydrated calcium aluminate, hydrated calcium ferraluminate, and hydrated calcium sulfoaluminate generated by fly ash, quicklime and water in a later period, and due to reduced air shrinkage, a good match with the original cultural relic is realized; and different proportions of active silica and active calcium oxide are added, due to different hydration and curing speeds, concrete materials with different workabilities are produced, and meanwhile, different types and contents of calcium compounds in hydration products can form concrete materials with different early strengths. Repairing concrete is prepared according to the formula of the concrete formulation system above, aiming at the first index value, the second index value, and the third index value of the cultural relic building concrete sample detected, concretes containing more fly ash or more lime or more gypsum or more other calcium compounds or more washed-out medium sand are prepared respectively, and concretes containing more silicate or more carbonate or more hydroxide are prepared respectively. Different types of concretes are prepared by adjusting a proportion of each component in the formula of the concrete formulation system.

DETAILED DESCRIPTION

The present invention is described in detail hereinafter with reference to the specific embodiments.

Embodiment 1

The present invention provided a concrete formulation system for repairing a cultural relic building and a use method thereof. The concrete formulation system consisted of a solid phase and a water phase; the solid phase and the water phase were mixed according to a mass percentage ratio of 1:0.5-2; and the solid phase consisted of 27 wt % to 95 wt % of gel matrix, 2 wt % to 40 wt % of active silica, and 2 wt % to 30 wt % of active calcium oxide.

The specific use method comprised the following steps.

At step 1, on-site sampling was performed, and a cultural relic building concrete sample was prepared.

At step 2, chemical components and contents of the cultural relic building concrete sample were detected by an XRF spectrometer and a Raman spectrometer, comprising: a fused piece and a pressed piece of the cultural relic building concrete sample were manufactured; a standard operation was performed by the XRF spectrometer and the Raman spectrometer, the fused piece and the pressed piece of the cultural relic building concrete sample were detected, and it was detected that components of cultural relic concrete contained calcium silicate and calcium sulfate; and it was detected by a regression analysis method that the amount of calcium silicate was 44 wt %, and the amount of calcium sulfate was 34 wt %.

At step 3, mass percentages of chemical components comprising magnesium oxide, aluminum oxide, and iron oxide were detected by a titration method, comprising: a sample solution with pH 1.8 was prepared and heated to 60° C.; then the sample solution was titrated to be bright yellow with an indicator and an EDTA standard titration solvent, and a volume of a titrant 1 used was recorded; a pH 3 sample solution was prepared and boiled; then the pH 3 sample solution was titrated to be bright yellow with an indicator and an EDTA standard titration solvent, and a volume of a titrant 2 used was recorded; and according to recorded data of the titrant 1 and the titrant 2, 10 wt % of magnesium oxide, 1 wt % of aluminum oxide, and 4 wt % of iron oxide were calculated.

At step 4, an average water penetration height value of the cultural relic building concrete sample was detected by a water penetration height method, comprising: a test piece of the cultural relic building concrete sample was manufactured; the sample test piece was mounted on an impermeability meter, water was injected to increase a pressure, and a water mark was drawn on a longitudinal section of the sample test piece after finishing water permeation; and water penetration height values of 12 water permeation points in the water mark were measured at equal intervals. Results are shown in Table 1, and the average water penetration height value was 38.6 mm.

TABLE 1

| | Number of points | | | | | | | | | | | | Average |
|---|---|---|---|---|---|---|---|---|---|---|---|---|---|
| | 1 | 2 | 3 | 4 | 5 | 6 | 7 | 8 | 9 | 10 | 11 | 12 | value |
| Water penetration height value | 37.9 | 38.4 | 40.4 | 41.3 | 39.8 | 39.2 | 38.6 | 37.7 | 37.4 | 37.3 | 37.4 | 37.8 | 38.6 |

At step 5, the 44 wt % of calcium silicate, the 34 wt % of calcium sulfate, the 10 wt % of magnesium oxide, the 1 wt % of aluminum oxide, the 4 wt % of iron oxide, and the average water penetration height of 38.6 mm measured were compared with a first index value, a second index value, and a third index value in a database of the concrete formulation system. Comparison results were that the first index value, the second index value, and the third index value were not greater than 20% of corresponding data sets, which were: 20 wt % to 40 wt % of calcium silicate, 20 wt % to 55 wt % of calcium sulfate, 3 wt % to 20 wt % of magnesium oxide, 1 wt % to 15 wt % of aluminum oxide, and a water penetration height of 17 mm to 39 mm. Raw material components and contents of cultural relic concrete were that a mass percentage ratio of silicate cement to gypsum was 0.5-1.2:0.5-2.0.

At step 6, silicate cement, gypsum, active calcium oxide, and active silicon dioxide were mixed at a mass percentage ratio of 1:1:0.1:0.1, and added with 1.5 times of water to prepare a repairing concrete sample 1.

At step 7, it was detected and analyzed by an XRF analyzer and a Raman spectrometer that the repairing concrete sample 1 contained 45 wt % of calcium silicate and 39 wt % of calcium sulfate; it was detected by the titration method that the repairing concrete sample 1 contained 9 wt % of magnesium oxide, 0.9 wt % of aluminum oxide, and 3.6 wt % of iron oxide; and water penetration height values of 12 water permeation points of the repairing concrete sample 1 were detected by a water penetration height method, as shown in Table 2, with an average water penetration height of 35.3 mm.

TABLE 2

| | Number of points | | | | | | | | | | | | Average |
|---|---|---|---|---|---|---|---|---|---|---|---|---|---|
| | 1 | 2 | 3 | 4 | 5 | 6 | 7 | 8 | 9 | 10 | 11 | 12 | value |
| Water penetration height value | 34.3 | 35.1 | 34.6 | 35.6 | 36.3 | 37.1 | 36.2 | 35.9 | 34.8 | 35.3 | 35.6 | 35.8 | 35.6 |

At step 8, comparing 45 wt % of calcium silicate and 39 wt % of calcium sulfate with 44 wt % of calcium silicate and 34 wt % of calcium sulfate, a difference was not greater than 20%; comparing 9 wt % of magnesium oxide, 0.9 wt % of aluminum oxide, and 3.6 wt % of iron oxide with 10 wt % of magnesium oxide, 1 wt % of aluminum oxide, and 4 wt % of iron oxide, a difference was not greater than 60%; and comparing an average water penetration height value of 35.3 mm with an average water penetration height value of 38.6 mm, a difference was not greater than 60%.

At step 9, the repairing concrete sample 1 was used to repair a cultural relic building corresponding to the cultural relic building concrete sample.

Embodiment 2

The present invention provided a concrete formulation system for repairing a cultural relic building and a use method thereof. The specific use method comprised the following steps.

At step 1, on-site sampling was performed, and a cultural relic building concrete sample was prepared.

At step 2, chemical components and contents of the cultural relic building concrete sample were detected by an XRF spectrometer and a Raman spectrometer, comprising: a fused piece and a pressed piece of the cultural relic building concrete sample were manufactured; a standard operation was performed by the XRF spectrometer and the Raman spectrometer, the fused piece and the pressed piece of the cultural relic building concrete sample were detected, and it was detected that components of cultural relic concrete contained calcium silicate and calcium sulfate; and it was detected by a regression analysis method that the amount of calcium silicate was 40 wt %, and the amount of calcium sulfate was 64 wt %.

At step 3, mass percentages of chemical components comprising magnesium oxide, aluminum oxide, and iron oxide were detected by a titration method, comprising: a sample solution with pH 1.8 was prepared and heated to 60° C.; then the sample solution was titrated to be bright yellow with an indicator and an EDTA standard titration solvent, and a volume of a titrant 1 used was recorded; a pH 3 sample solution was prepared and boiled; then the pH 3 sample solution was titrated to be bright yellow with an indicator and an EDTA standard titration solvent, and a volume of a titrant 2 used was recorded; and according to recorded data of the titrant 1 and the titrant 2, 7 wt % of magnesium oxide, 1.1 wt % of aluminum oxide, and 3 wt % of iron oxide were calculated.

At step 4, an average water penetration height value of the cultural relic building concrete sample was detected by a water penetration height method, comprising: a test piece of the cultural relic building concrete sample was manufactured; the sample test piece was mounted on an impermeability meter, water was injected to increase a pressure, and a water mark was drawn on a longitudinal section of the sample test piece after finishing water permeation; and water penetration height values of 12 water permeation points in the water mark were measured at equal intervals. Results are shown in Table 3, and the average water penetration height value was 29.4 mm.

TABLE 3

| | Number of points | | | | | | | | | | | | Average |
|---|---|---|---|---|---|---|---|---|---|---|---|---|---|
| | 1 | 2 | 3 | 4 | 5 | 6 | 7 | 8 | 9 | 10 | 11 | 12 | value |
| Water penetration height value | 28.6 | 29.4 | 29.8 | 30.5 | 30.8 | 31.4 | 29.5 | 29.7 | 28.6 | 28.1 | 27.9 | 27.9 | 29.4 |

At step 5, the 40 wt % of calcium silicate, the 64 wt % of calcium sulfate, the 7 wt % of magnesium oxide, the 1.1 wt % of aluminum oxide, the 3 wt % of iron oxide, and the average water penetration height of 29.4 mm measured were compared with a first index value, a second index value, and a third index value in a database of the concrete formulation system. Comparison results were that the first index value, the second index value, and the third index value were not greater than 20% of corresponding data sets, which were: 20 wt % to 40 wt % of calcium silicate, 20 wt % to 55 wt % of calcium sulfate, 3 wt % to 20 wt % of magnesium oxide, 1 wt % to 15 wt % of aluminum oxide, and a water penetration height of 17 mm to 39 mm. Raw material components and contents of cultural relic concrete were that a mass percentage ratio of silicate cement to gypsum was 0.5-1.2:0.5-2.0.

At step 6, silicate cement and gypsum were mixed at a mass percentage ratio of 1:1, and added with 1 times of water to prepare a repairing concrete sample 1.

At step 7, it was detected and analyzed by an XRF analyzer and a Raman spectrometer that the repairing concrete sample 1 contained 39 wt % of calcium silicate and 41 wt % of calcium sulfate; it was detected by the titration method that the repairing concrete sample 1 contained 5 wt % of magnesium oxide, 1.2 wt % of aluminum oxide, and 3.5 wt % of iron oxide; and water penetration height values of 12 water permeation points of the repairing concrete sample 1 were detected by a water penetration height method, as shown in Table 4, with an average water penetration height of 32.8 mm.

TABLE 4

| | Number of points | | | | | | | | | | | | Average |
|---|---|---|---|---|---|---|---|---|---|---|---|---|---|
| | 1 | 2 | 3 | 4 | 5 | 6 | 7 | 8 | 9 | 10 | 11 | 12 | value |
| Water penetration height value | 32.5 | 31.8 | 32.6 | 33.4 | 33.9 | 33.6 | 33.6 | 32.8 | 32.4 | 31.9 | 32.3 | 32.8 | 32.8 |

At step 8, comparing 39 wt % of calcium silicate and 41 wt % of calcium sulfate with 40 wt % of calcium silicate and 64 wt % of calcium sulfate, a difference was greater than 20%; comparing 5 wt % of magnesium oxide, 1.2 wt % of aluminum oxide, and 3.5 wt % of iron oxide with 7 wt % of magnesium oxide, 1.1 wt % of aluminum oxide, and 3 wt % of iron oxide, a difference was greater than 60%; and comparing an average water penetration height value of 32.8 mm with an average water penetration height value of 29.4 mm, a difference was greater than 60%.

At step 9, mass percentages of raw material components in the repairing concrete sample 1 were adjusted, silicate cement, gypsum, active calcium oxide, and active silicon dioxide were mixed at a mass percentage ratio of 0.7:1.8:0.3:0.3, and added with 1 times of water to prepare a repairing concrete sample 2.

At step 10, it was detected by an XRF analyzer and a Raman spectrometer that the re-prepared repairing concrete sample 2 contained 36 wt % of calcium silicate and 52 wt % of calcium sulfate; it was detected by the titration method that the re-prepared repairing concrete sample 2 contained 4 wt % of magnesium oxide, 1.4 wt % of aluminum oxide, and 3 wt % of iron oxide; and water penetration height values of 12 water permeation points of the re-prepared repairing concrete sample 2 were detected by the water penetration height method, as shown in Table 5, with an average water penetration height of 28.5 mm.

TABLE 5

| | Number of points | | | | | | | | | | | | Average value |
|---|---|---|---|---|---|---|---|---|---|---|---|---|---|
| | 1 | 2 | 3 | 4 | 5 | 6 | 7 | 8 | 9 | 10 | 11 | 12 | |
| Water penetration height value | 28.6 | 28.4 | 28.7 | 29.1 | 29.3 | 28.6 | 28.2 | 27.8 | 28.1 | 28.2 | 28.3 | 28.5 | 28.5 |

At step 11, comparing 36 wt % of calcium silicate and 52 wt % of calcium sulfate with 40 wt % of calcium silicate and 64 wt % of calcium sulfate, a difference was not greater than 20%; comparing 4 wt % of magnesium oxide, 1.4 wt % of aluminum oxide, and 3 wt % of iron oxide with 7 wt % of magnesium oxide, 1.1 wt % of aluminum oxide, and 3 wt % of iron oxide, a difference was not greater than 60%; and comparing an average water penetration height value of 28.5 mm with an average water penetration height value of 29.4 mm, a difference was not greater than 60%.

At step 12, the new repairing concrete sample 2 was used to repair a cultural relic building corresponding to the cultural relic building concrete sample.

To sum up, when comparison results are that a difference between the first index values of the repairing concrete sample and the cultural relic building concrete sample is not greater than 20%, a difference between the second index values is not greater than 60%, and a difference between the third index values is not greater than 60%, the prepared repairing concrete sample meets requirements, and has components and properties similar to those of the cultural relic building concrete sample, and the repairing concrete sample may be used to repair the cultural relic corresponding to the cultural relic building concrete sample, so that the raw material formula of the original old material is restored, and a purpose of repairing with "a original material by an original workmanship" and maintaining "cultural importance" is achieved.

Those described above are only exemplary embodiments of the present invention, but are not intended to limit the present invention. Any modifications, equivalent substitutions and improvements made without departing from the spirit and principle of the present invention shall all fall within the scope of protection of the present invention.

The invention claimed is:

1. A concrete formulation system for repairing a cultural relic building and a use method thereof, wherein the concrete formulation system consists of a solid phase and a water phase, and the solid phase and the water phase are mixed according to a mass percentage ratio of 1:0.5-2; the solid phase consists of a gel matrix and an additive, comprising 0.1% to 99.9% of gel matrix and 99.9% to 0.1% of additive, wherein the gel matrix is at least one selected from the group consisting of cement, volcanic ash, fly ash, gypsum, silica fume, kaolin, metakaolin, diatomite, slag powder, siliceous slag powder and burnt clay; and the additive comprises at least one selected from the group consisting of lime, aggregate, active silica, active calcium oxide, active magnesium oxide, calcium bicarbonate, silicic acid and titanium oxide;

and making a database of the concrete formula system using the concrete formula system, the database comprises the first index value, the second index value, and the third index value; the first index value is the mass percentage value of silicate and/or hydroxide and/or carbonate and/or sulfate and/or ferraluminate and/or aluminate and/or sulfoaluminate and/or chloride in concrete detected and analyzed by the spectrum analyzer; the second index value is the chloride ion migration coefficient and/or the average carbonization degree value and/or the mass percentage value of oxide of concrete detected and analyzed by the chemical analysis method; and the third index value is the strength value and/or the early strength value and/or the porosity and/or the elasticity value and/or the creep value and/or the volume change value and/or the frost resistance value and/or the average water penetration height value of concrete detected and analyze by the mechanical analysis method;

and the use method comprises the following steps of:

S1: obtaining a cultural relic building concrete sample;

S2: obtaining a first index value of the cultural relic building concrete sample, wherein the first index value is a mass percentage value of silicate and/or hydroxide and/or carbonate and/or sulfate and/or ferraluminate and/or aluminate and/or sulfoaluminate and/or chloride in concrete detected and analyzed by a spectrum analyzer;

S3: obtaining a second index value of the cultural relic building concrete sample, wherein the second index value is a chloride ion migration coefficient and/or an average carbonization degree value and/or a mass percentage value of oxide of concrete detected and analyzed by a chemical analysis method;

S4: obtaining a third index value of the cultural relic building concrete sample, wherein the third index value is a strength value and/or an early strength value and/or a porosity and/or an elasticity value and/or a creep value and/or a volume change value and/or a frost resistance value and/or an average water penetration height value of concrete detected and analyze by a mechanical analysis method;

S5: comparing the first index value, the second index value, and the third index value of the cultural relic building concrete sample with a first index value, a second index value, and a third index value in a database of the concrete formulation system, when the first index value, the second index value and the third index value of the concrete formula obtained from the database of the concrete formula system are not more than 20% different from the first index value, the second index value and the third index value of the concrete sample of cultural relics, the raw material composition and content of the corresponding concrete formula are recorded;

wherein the raw material composition and content of the corresponding concrete formula is the raw material composition and content of the cultural relics building concrete;

S6: according to the raw material components and contents of the cultural relic concrete obtained in step S5, using materials of the concrete formulation system to prepare a repairing concrete sample;

S7: respectively detecting and analyzing the first index value, the second index value, and the third index value of the repairing concrete sample by the spectrum analyzer, the chemical analysis method, and the mechanical analysis method, and comparing and analyzing the first index value, the second index value, and the third index value of the repairing concrete sample with the first index value, the second index value, and the third index value of the cultural relic building concrete sample detected and analyzed in step S2 to step S4;

S8: if comparison and analysis results are that a difference between the first index values of the repairing concrete sample and the cultural relic building concrete sample is greater than 20% and/or a difference between the second index values is greater than 60% and/or a difference between the third index values is greater than 60%, then according to the concrete formulation system, adjusting material components and mass percentages of the repairing concrete sample, preparing the repairing concrete sample with the adjusted material components and contents, and repeating step S7; and S9: if comparison and analysis results are that a difference between the first index values of the repairing concrete sample and the cultural relic building concrete sample is not greater than 20%, a difference between the second index values is not greater than 60%, and a difference between the third index values is not greater than 60%, using the repairing concrete sample for cultural relic repair.

2. The concrete formulation system for repairing the cultural relic building and the use method thereof according to claim 1, wherein the solid phase consists of 0.1% to 99.9% of gel matrix, 0.01 wt % to 85 wt % of lime, 0.01 wt % to 70 wt % of aggregate, 0.01 wt % to 4 0 wt % of active silica, 0.01 wt % to 30 wt % of active calcium oxide, 0.01 wt % to 5 wt % of active magnesium oxide, 0.01 wt % to 20 wt % of calcium bicarbonate, 0.01 wt % to 10 wt % of silicic acid, and 0.01 wt % to 10 wt % of titanium oxide.

3. The concrete formulation system for repairing the cultural relic building and the use method thereof according to claim 1, wherein the aggregate is at least one selected from the group consisting of washed-out medium sand, washed-out coarse sand and stone chip.

4. The concrete formulation system for repairing the cultural relic building and the use method thereof according to claim 1, wherein the spectrum analyzer is an XRF analyzer or an X-ray diffractometer or a laser-induced breakdown spectrometer or a Raman spectrometer; the chemical analysis method is an ignition subtraction method or a titration method or a rapid determination method of chloride ion diffusion coefficient of concrete and a phenolphthalein test method; and the mechanical analysis method is a shear compression method or a creep test method or a water penetration height method.

5. The concrete formulation system for repairing the cultural relic building and the use method thereof according to claim 1, wherein the active silica is nano silica, and the active calcium oxide is nano calcium oxide.

* * * * *